US00PP31831P2

(12) United States Plant Patent
Eveleens et al.

(10) Patent No.: US PP31,831 P2
(45) Date of Patent: Jun. 2, 2020

(54) ***HYDRANGEA* PLANT NAMED 'HOKOMAFATA'**

(50) Latin Name: *Hydrangea macrophylla*
Varietal Denomination: Hokomafata

(71) Applicants: Horteve Breeding BV, Aalsmeer (NL); Kolster Holding BV, Boskoop (NL)

(72) Inventors: Cornelis Pieter Eveleens, Aalsmeer (NL); Peter Rudolf Kolster, Boskoop (NL)

(73) Assignees: HORTEVE BREEDING B.V., Aalsmeer (NL), part interest; KOLSTER HOLDING B.V., Boskoop (NL), part interest ( * ) Notice: Subject to any disclaimer, the term of this patent is extended or adjusted under 35 U.S.C. 154(b) by 0 days.

(21) Appl. No.: 16/501,836

(22) Filed: Jun. 14, 2019

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./263.1, 250
See application file for complete search history.

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of *Hydrangea macrophylla* plant named 'Hokomafata' that is characterized by its picotee flowers with creamy white centers and a red-pink margin, its very floriferous blooming habit, its green leaves with a hint of brown, and its suitability as a potted plant.

2 Drawing Sheets

Botanical classification: *Hydrangea macrophylla.*
Varietal denomination: 'Hokomafata'.

CROSS REFERENCE TO RELATED APPLICATIONS

This application is related to U.S. Plant Patents for a plant derived from the same breeding program that are entitled *Hydrangea* Plant Named 'Hortfire' (U.S. Pat. No. 29,058) and *Hydrangea* Plant Named 'Horthamp' (U.S. Plant Pat. No. 29,005).

BACKGROUND OF THE INVENTION

The present invention relates to a new and distinct cultivar of *Hydrangea macrophylla* and will be referred to hereafter by its cultivar name, 'Hokomafata'. 'Hokomafata' represents a new bigleaf *hydrangea*, a perennial shrub grown for landscape use and as a potted plant.

'Hokomafata' derived from an ongoing controlled breeding program directed by the Inventors. An objective of the breeding program included developing a new cultivar of *Hydrangea* with picotee flowers, a good flowering habit and other desirable traits.

'Hokomafata' arose from a controlled cross made by the Inventor in Boskoop, The Netherlands in June of 2011 between unnamed and unpatented proprietary plants in the Inventor's breeding program; reference no. 07-120-09 as the female parent and reference no. 09-001-04 as the male parent. 'Hokomafata' was selected as a single unique plant from amongst the resulting seedlings in June of 2013.

Asexual propagation of the new cultivar was first accomplished by stem cuttings by one of the Inventors in August of 2013 in Boskoop, The Netherlands. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Hokomafata' as a unique cultivar of *Hydrangea macrophylla.*

1. 'Hokomafata' exhibits picotee flowers with creamy white centers and a red-pink margin.
2. 'Hokomafata' exhibits a very floriferous blooming habit.
3. 'Hokomafata' exhibits green leaves with a hint of brown.
4. 'Hokomafata' exhibits suitability as a potted plant.

The female parent of 'Hokomafata' differs from 'Hokomafata' in having flowers that are lighter in color with a smaller red sepal edge, lighter color leaves and a smaller sized inflorescence. The male parent of 'Hokomafata' differs from 'Hokomafata' in having lighter color leaves, a red sepal edge that is smaller and sepal that are held flatter. 'Hokomafata' can be most closely compared to the *Hydrangea macrophylla* cultivars 'Hortfire' and 'Horthamp'. 'Hortfire' is similar to 'Hokomafata' in having picotee flowers and leaves that are green in color with a hint of brown. 'Hortfire' differs from 'Hokomafata' in having longer branches, more flowers per inflorescence with sepals with more deeply crenate margins. 'Horthamp' is similar to 'Hokomafata' in having picotee flowers, leaves that are green in color with a hint of brown and an upright plant habit. 'Horthamp' differs from 'Hokomafata' in having flowers that are more red in color with the color distributed gradually across the flowers and leaves with more deeply crenate margins.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date.

BRIEF DESCRIPTION OF THE DRAWINGS

The accompanying colored photographs illustrate the overall appearance and distinct characteristics of the new *Hydrangea*. The photographs were taken of a three-year-old plant of 'Hokomafata' as grown in a greenhouse in a 17-cm container in Boskoop, The Netherlands.

The photograph in FIG. 1 provides a side view of the plant habit of 'Hokomafata' in bloom.

Figure 1:
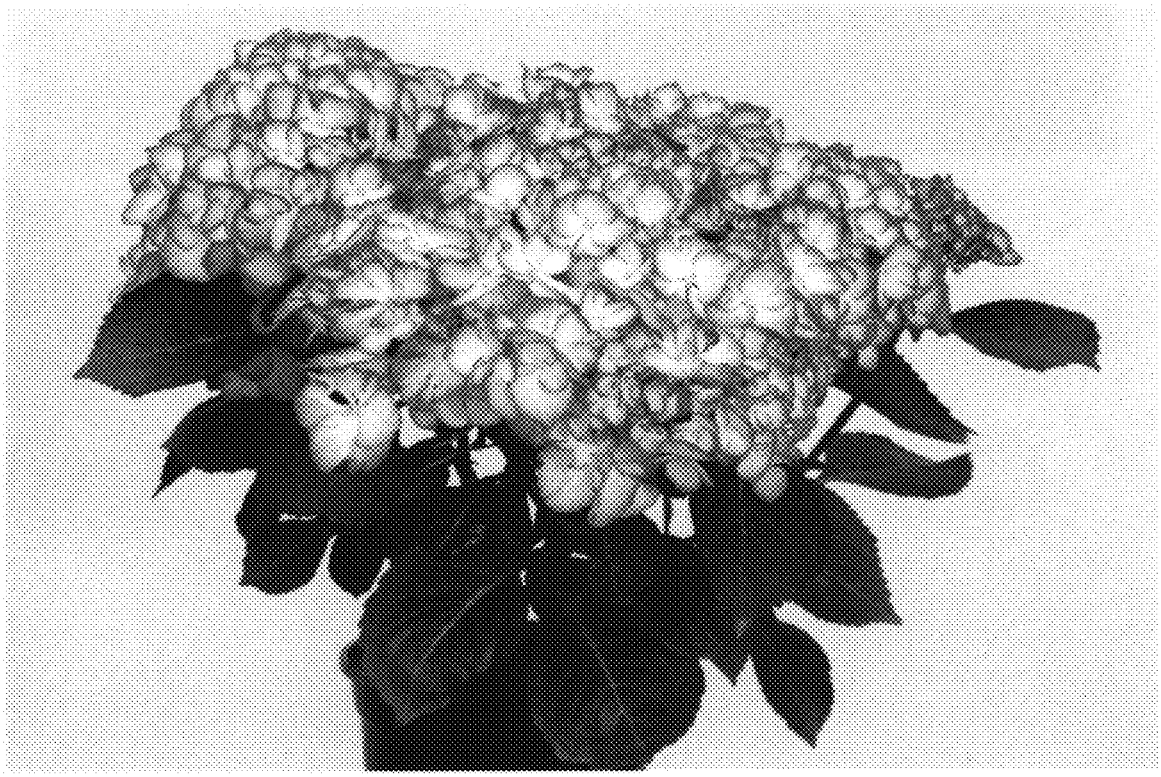
Figure 2:
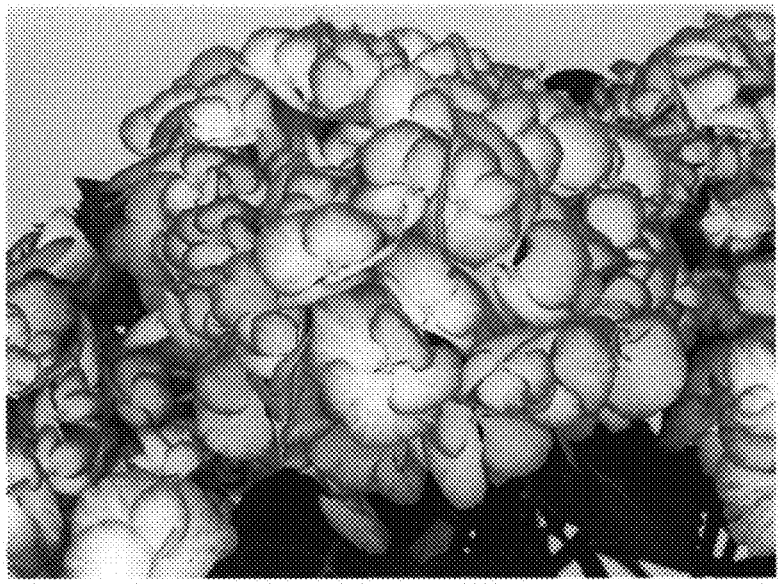

The photograph in FIG. 2 provides a close-up view of a fully open inflorescence of 'Hokomafata'.

Figure 3:
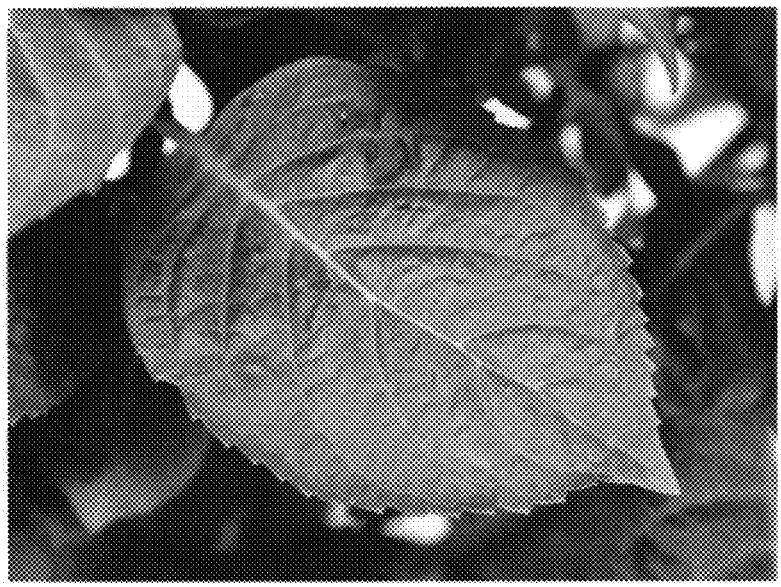

The photograph in FIG. 3 provides a close-up view of the foliage of 'Hokomafata'.

The colors in the photographs are as close as possible with the photographic and printing technology utilized and the color values cited in the detailed botanical description accurately describe the colors of the new *Hydrangea*.

BOTANICAL DESCRIPTION OF THE PLANT

The following is a detailed description of three-year-old plants of 'Hokomafata' as grown in a greenhouse in 17-cm containers in Boskoop, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Late spring to late summer with flowers showy at least for 2 months in the Netherlands.

*Plant type*.—Deciduous shrub, mophead type *Hydrangea*.

*Plant habit*.—Broad spreading, upright, compact.

*Height and spread*.—An average of 36.1 cm in in height and 51.5 cm in spread as grown in a 17-cm container, reaches 1 m in height and spread as a 3-year-old plant in the landscape.

*Hardiness*.—At least U.S.D.A. Zones 5 to 9.

*Diseases and pests*.—No susceptibility and resistance to diseases or pests has been observed.

*Root description*.—Fine and fibrous, 161C in color.

*Propagation*.—Stem cuttings.

*Root development*.—An average of 6 weeks for root initiation with a young rooted plant produced in an average of 18 weeks.

*Growth rate and vigor*.—Moderate.

Stem description:

*Stem shape*.—Rounded.

*Stem strength*.—Strong.

*Stem color*.—Young and mature growth; 143B to 144A.

*Stem size*.—An average of 17.1 cm in length (excluding inflorescence) and 7 mm in diameter.

*Stem surface*.—Glabrous, sparsely lenticellate, lenticels; an average of 3 mm in length and 0.5 mm in diameter, 187A in color, bark; moderately rough with fissures.

*Stem aspect*.—Upright, held in an average angle of 52° to the soil, varying between 40° and 65°.

*Internode length*.—An average of 5 cm.

*Branching*.—Freely branching with an average of 10 lateral branches.

Foliage description:

*Leaf shape*.—Broad ovate to elliptic.

*Leaf arrangement*.—Opposite.

*Leaf division*.—Simple.

*Leaf base*.—Short attenuate.

*Leaf apex*.—Apiculate.

*Leaf margins*.—Serrate to coarsely serrate.

*Leaf venation*.—Pinnate, color; color upper surface 144A, lower surface 145B.

*Leaf size*.—An average of 11.6 cm in length and 8.3 cm in width.

*Leaf attachment*.—Petiolate.

*Leaf number*.—An average of 8 per lateral stem.

*Leaf surface*.—Both surfaces; glabrous and slightly rugose, lower side is very sparsely pubescent on secondary veins and on vein axils, average of 0.2 mm in length and too small to measure color but closest to NN155D.

*Leaf color*.—Young foliage; upper surface 141A, strongly tinged 200A towards the margins, lower surface 197A to 197B, mature foliage; upper surface between NN137A and 147A, slightly tinged 200A at the margins, lower surface 147B to 148B.

*Petioles*.—An average of 1.9 cm in length and 3.5 mm in diameter, upper surface 145A in color, lower surface 144B in color, surface glabrous and moderately glossy.

Inflorescence description:

*Inflorescence type*.—Terminal panicle, rounded mophead comprised of a sterile flowers above fertile flowers.

*Lastingness of inflorescence*.—Sterile flowers; persistent for an average of 6 weeks, fertile flowers; persistent, do not open and dry out before opening.

*Inflorescence number*.—One per lateral stem.

*Inflorescence size*.—An average of 15.3 cm in height and 19.9 cm in diameter.

*Flower number*.—An average of 125 sterile flowers and 50 fertile flowers per panicle.

*Flower fragrance*.—None.

*Flower aspect*.—Upright to outward.

*Flower size*.—Sterile flowers; an average of 4.4 cm in diameter and 1.4 cm in depth, fertile flowers; an average of 5 mm in diameter and 3 mm in depth.

*Flower type*.—Rotate.

*Flower buds*.—Sterile flowers; an average of 9 mm in length and 1 cm in diameter, narrow, cup shaped, 145B, margined 46A, fertile flowers; an average of 5 mm in length and 3 mm in diameter, obovate in shape, color; 145D, 144B at base, upper portion 185B.

*Peduncles*.—Strong, flattened oval in shape, an average of 2 cm in length and 2.3 mm in width on primary peduncles and secondary peduncles 1 cm in length and 2 mm in width, 183A and 185A in color, dull and densely pubescent surface covered with thin pubescence an average of 0.2 mm in length and too small to measure color.

*Pedicels*.—Sterile flowers; held primarily at an average angle of 35° to upright from peduncle, an average of 2 cm in length and 1.5 mm in diameter, moderately strong strength, color; 155C, changing to 183A and 185A at the proximal end, dull and densely pubescent surface covered with thin pubescence an average of 0.2 mm in length and too small to measure color, fertile flowers; held at an average angle of 10° from vertical, an average of 3 mm in length and 1 mm in diameter, moderate strength, 150D in color, glabrous and dull surface.

*Petals*.—Sterile flowers; an average of 4 (occasionally 3 to 5) rotate, cruciform in arrangement, acute apex, cuneate base, entire margins, ovate in shape, concave in aspect, average of 3.5 mm in length and 2 mm in width, both surfaces; glabrous and dull, color; when opening upper surface 157D, changing to 54B at the top, when opening lower surface 157D, changing to 54A at the top, when fully open upper surface 157D, changing to 54B, when fully open lower surface 157D changing to 54A, fertile flowers; an average of 4, rotate in arrangement and not opening and drying out before fully open, ovate and concave in shape, entire margin, acute apex, cuneate base, an average of 3.5 mm in length and 2 mm in width, upper and lower surface glabrous and dull, color; upper surface when opening 157D, changing to 54B at the top, lower surface when opening 157D, changing to 54A at the top, fully open colors are not observed as flowers do not fully open, dry out and drop.

*Sepals*.—Sterile flowers; 4 to 5, rotate, cruciform arrangement, un-deeply emarginate to obtuse apex, cuneate base, entire margins that are slightly to moderately undulate, reniform in shape and slightly wavy and concave, an average of 2.6 cm in length and 3 cm in width, both surfaces glabrous and dull, lower surface sparsely pubescent an average of 0.2 mm in length and too small to measure color with color chart, color; when opening upper surface between 150D and 157A, changing to 53C to 53D at the margins, when opening lower surface 150D, changing to 53C at the margins, outer edge 53A, when fully open NN155B, changing to 50A at the margins, fading to 144A, margins 46A to 46B, when fully open lower surface 51A, changing to NN155A at the base, fading to 144B, margins 53B, fertile flowers; an average of 5, deltoid in shape, entire margin, broad acute apex, 1.5 mm in length and width, and broad cuneate base, both surfaces are glabrous and dull, color; upper and lower surface when opening and fully opened 144B to 144C.

Reproductive organs:

*Presence*.—Flowers dropped when mature, gynoecium and androecium not developed.

*Fruit and seed*.—None observed to date as reproductive organs do not mature.

It is claimed:

1. A new and distinct cultivar of *Hydrangea* plant named 'Hokomafata' substantially as herein illustrated and described.

* * * * *